United States Patent [19]

Ito

[11] Patent Number: 4,532,039
[45] Date of Patent: * Jul. 30, 1985

[54] MULTI-LAYER COIL ASSEMBLY COAXIALLY MOUNTED AROUND THE ROTARY AXIS FOR PREPARATORY COUNTERCURRENT CHROMATOGRAPHY

[75] Inventor: Yoichiro Ito, Bethesda, Md.

[73] Assignee: The United States of America as represented by the Secretary of the Department of Health and Human Services, Washington, D.C.

[*] Notice: The portion of the term of this patent subsequent to Feb. 7, 2001 has been disclaimed.

[21] Appl. No.: 475,215

[22] Filed: Mar. 14, 1983

[51] Int. Cl.³ ............................................. B01N 15/08
[52] U.S. Cl. ............................................. 210/198.2; 210/511
[58] Field of Search ............................ 494/31, 35, 45, 85; 210/635, 657, 198.2, 511

[56] References Cited

U.S. PATENT DOCUMENTS

| | | | |
|---|---|---|---|
| 3,856,669 | 12/1974 | Ito et al. | 210/635 |
| 4,051,025 | 9/1977 | Ito | 210/198.2 |
| 4,058,460 | 11/1977 | Ito | 210/198.2 |
| 4,228,009 | 10/1980 | Ito | 494/85 X |
| 4,321,138 | 3/1982 | Ito | 210/198.2 |
| 4,324,661 | 4/1982 | Ito | 210/198.2 |
| 4,430,216 | 2/1984 | Ito | 210/198.2 |

OTHER PUBLICATIONS

Ito, Y., *J. of Chromatography* "New Continuous Extraction Method with a Coil Planet Centrifuge," 207 (1981) 161–169.

*Primary Examiner*—Richard V. Fisher
*Assistant Examiner*—W. Gary Jones
*Attorney, Agent, or Firm*—Browdy and Neimark

[57] ABSTRACT

A horizontal flow-through apparatus for countercurrent chromatography consisting of a horizontal multi-layer helically coiled column coaxially carried on a flanged spool which is rotated around its own axis in a frame which is simultaneously rotated by a motor about the same main axis. The column assembly rotates at a rate twice that of the rotary frame in the same direction, the arrangement being such that the inlet and outlet flow tubes are twist-free. The effluent through the outlet tube of the column is continuously monitored by a UV monitor and then fractionated into test tubes by a fraction collector. The apparatus is driven by the motor, which is drivingly connected to the frame on the main axis, and the column assembly is driven by gearing via a countershaft journalled in the frame and having a toothed pulley drivingly coupled by a toothed belt to a fixed toothed pulley coaxial with the column.

10 Claims, 4 Drawing Figures

MULTI-LAYER COIL ASSEMBLY COAXIALLY MOUNTED AROUND THE ROTARY AXIS FOR PREPARATORY COUNTERCURRENT CHROMATOGRAPHY

FIELD OF THE INVENTION

This invention relates to continuous countercurrent chromatography systems, and more particularly to an improved system for continuous countercurrent chromatography which employs a horizontal multi-layer helically-coiled tubular array rotating on its longitudinal axis.

BACKGROUND OF THE INVENTION

The principle of countercurrent chromatography (CCC) is generally as follows: when a water-filled coil is held horizontal and slowly rotated around its own axis, any object therein either heavier or lighter than the water moves toward one end of the coil. This end is called the "head" and the other end the "tail" of the coil. When such a coil contains two immiscible solvents, slow rotation soon establishes a hydrodynamic equilibrium between the two solvent phases where the head side of the coil is occupied by nearly equal amounts of the two phases and any excess of either phase is found at the tail end of the coil. Under this hydrodynamic equilibrium condition, the coil can be eluted with one of the phases through the head end while retaining the other phase stationary in the coil. Consequently, solutes locally introduced at the head of the coil are subjected to an efficient partition process between the mobile and stationary phases and chromatographically separated according to their partition coefficients in the absence of solid supports. Eluate through the tail end of the coil is continuously monitored as to optical absorbance and then is fractionated, as in liquid chromatography.

Peak resolution produced by this CCC scheme is greatly influenced by volume of the stationary phase retained in the coil, i.e., the higher the retention level, the better is the result obtained. It has been observed that the retention of the stationary phase is quite sensitive to the orientation and rotational speed of the coil. In the coaxially rotated coil, slow rotation usually yields nearly 50% retention. Increase of the rotational speed of the coil radically changes the hydrodynamic equilibrium volume ratio of the two phases in the coil, and in some critical range, one of the phases almost entirely collects at the head end and the other phase at the tail end of the coil.

This equilibrium condition permits a high retention level of the stationary phase if the mobile phase is introduced in the proper direction. In the eccentric orientation of the coil, the centrifugal force field induced by the rotation tends to trap the heavier phase in the outer half and the lighter phase in the inner half of each helical turn, resulting in more or less even distribution of the two phases throughout the coil and, therefore, the retention of the stationary phase becomes rather insensitive to the rotational rate of the coil. Thus, eccentrically rotated coils usually retain the stationary phase in no more than 50% of the column space unless the axis of rotation is inclined relative to the horizontal plane.

In the prior art, countercurrent chromatography has been performed by the use of multiple units of individually wound coils eccentrically attached to and supported by a rotary shaft. Each coil unit was equipped with connectors at both ends, and a long column was made by connecting the desired number of these coil units in series. This column arrangement, however, usually retains the stationary phase at a level less than 50% of the total free space in the column. The retention of the stationary phase is an important parameter for determining the degree of peak resolution and the sample loading capacity.

More specifically, it is known that performance of CCC systems mainly depends upon the amount of the stationary phase retained in the column, which determines both the resolving power of the solute peaks and the sample loading capacity. Various CCC systems developed in the past (see Y. Ito, J. Biochem. Biophys. Met., 5 (1981) 105) are usually capable of yielding retention of the stationary phase of no more than 50% of the total column space. This maximum attainable retention level tends to fall rather sharply with the application of higher flow rates of the mobile phase, resulting in loss of peak resolution. Consequently, the applicable flow rate has become one of the major limiting factors in CCC, and the prior methods require relatively long separation times, ranging from overnight to several days to complete a sizable separation. There is a definite need for an improved CCC system which can perform using a relatively high feed rate of the sample solution and which requires a substantially shortened separation time (see Y. Ito, J. Chromatogr., 207 (1981) 161).

SUMMARY OF THE INVENTION

As a result of efforts made to develop an improved CCC system which performs efficient extraction with a high feed rate of the sample solution, it has been found advantageous to employ a new configuration of the column, consisting of multiple layers of the coil, namely, multiple layers of tubing helically wound on a spool, and this coil configuration was found to retain a large volume of the stationary phase if this column was coaxially mounted on the rotary support. This arrangement provides a number of important advantages over the prior art systems, including the following;

1. The multi-layer coil provides much higher peak resolution;
2. It has a greater sample loading capacity;
3. It does not employ junctions within the column and therefore provides a leak-free system;
4. It is easily fabricated and is inexpensive; and
5. It is more compact than the apparatus used in the prior art systems and thus saves space in the laboratory.

Accordingly, a main object of the present invention is to provide an improved CCC system which overcomes the deficiencies and disadvantages of the previously employed horizontal CCC systems.

A further object of the invention is to provide an improved CCC system of the horizontally rotating column type allowing a relatively high flow rate of the mobile phase under the unit gravitational field.

A still further object of the invention is to provide an improved CCC system of the horizontally rotating column type which employs a multi-layer coiled column which gives much higher peak resolution than the rotating column structures employed in prior systems.

A still further object of the invention is to provide an improved CCC system which employs a multi-layer coiled, horizontally rotating column providing increased sample loading capacity as compared with prior systems, and which is substantially leak-free.

A still further object of the invention is to provide an improved CCC system employing a coaxially rotating multi-layer coiled separation column which is easy and inexpensive to fabricate, which is compact in size, and which is substantially dynamically balanced so that it is unnecessary to employ counterweight means to establish such balance.

A still further object of the invention is to provide an improved CCC system employing a coaxially rotating multi-layer helically coiled separation column which is driven to rotate at an optimum rate around its longitudinal axis and which is employed in a continuous flow system without requiring the use of rotating seals, and wherein the mobile phase and sample are pumped at a relatively high flow rate through the column while the column is rotating at said optimum rate, and wherein the effluent through the outlet of the column is continuously monitored with a UV monitor and then fractionated into receptacles by a fraction collector.

A still further object of the invention is to provide an improved horizontal CCC flow-through system using a multi-layer coiled coaxially rotating column which can retain a large volume of the stationary phase against a high flow rate of the mobile phase, enabling separation to be completed within reasonable time periods, as compared with longer times required for such separation using previously known systems for performing such separations.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
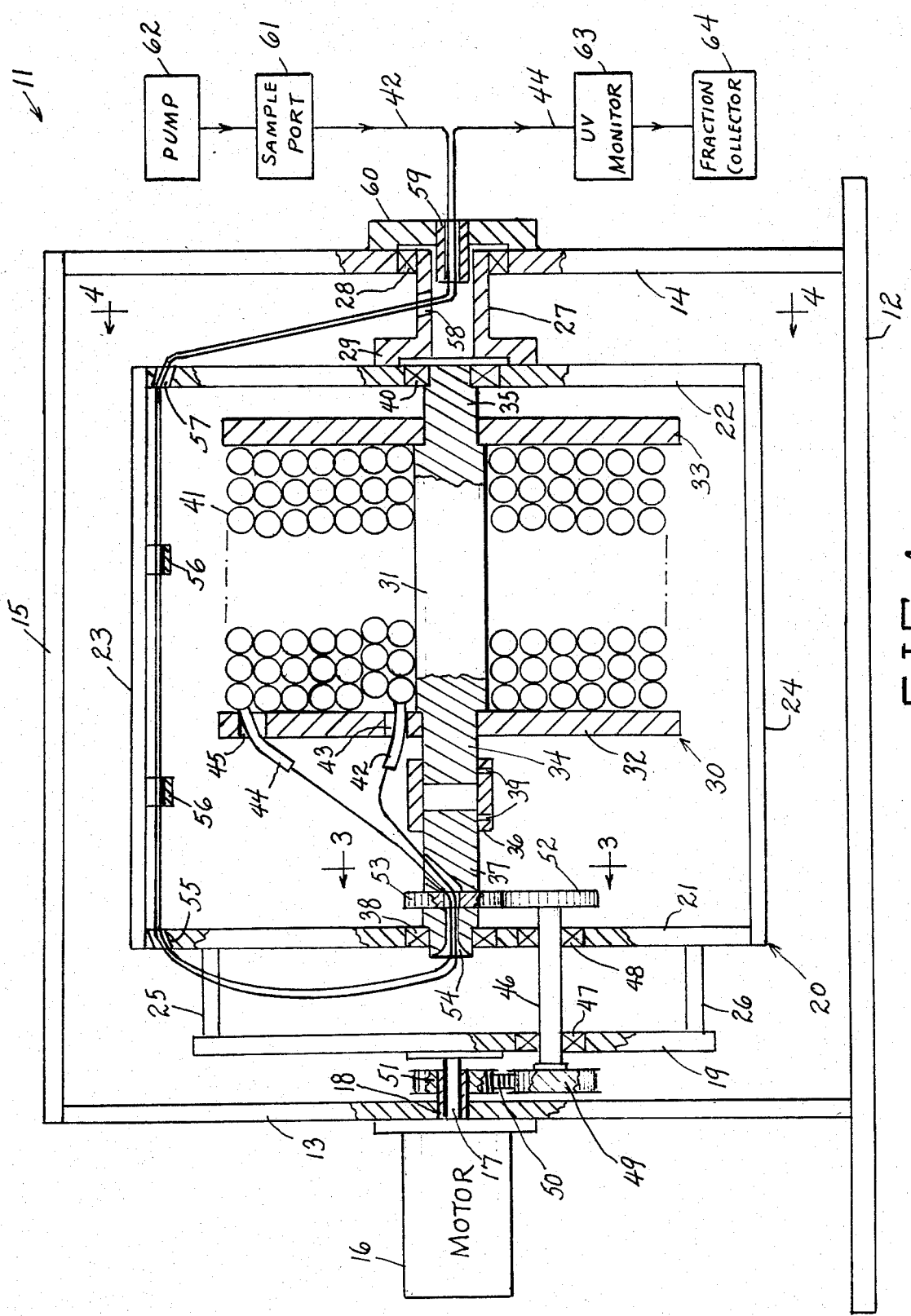
FIG. 1 is a detailed vertical cross-sectional view, partly in elevation, taken through an improved multi-layer coiled column countercurrent chromatography system constructed in accordance with the present invention.
Figure 2:
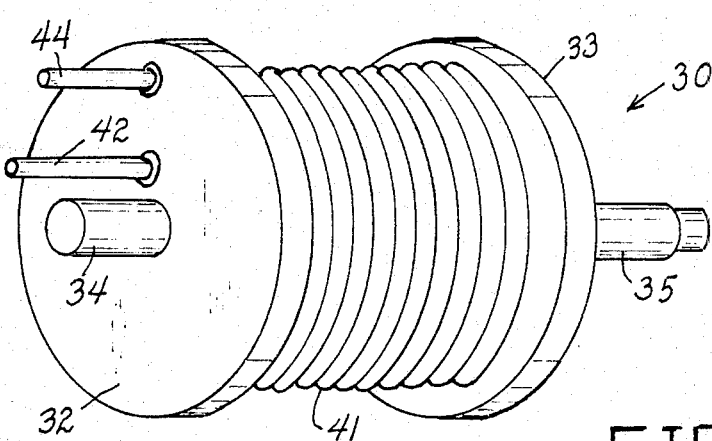
FIG. 2 is a perspective view of a multi-layer coiled column assembly such as that employed in the system shown in FIG. 1.
Figure 3:
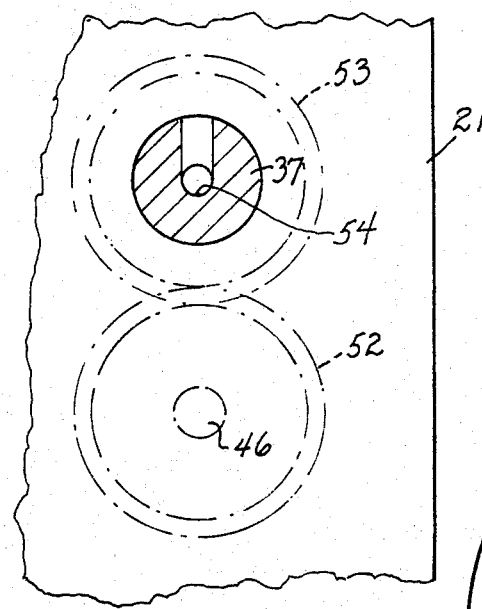
FIG. 3 is an enlarged fragmentary transverse vertical cross-sectional view taken substantially on the line 3—3 of FIG. 1.
Figure 4:
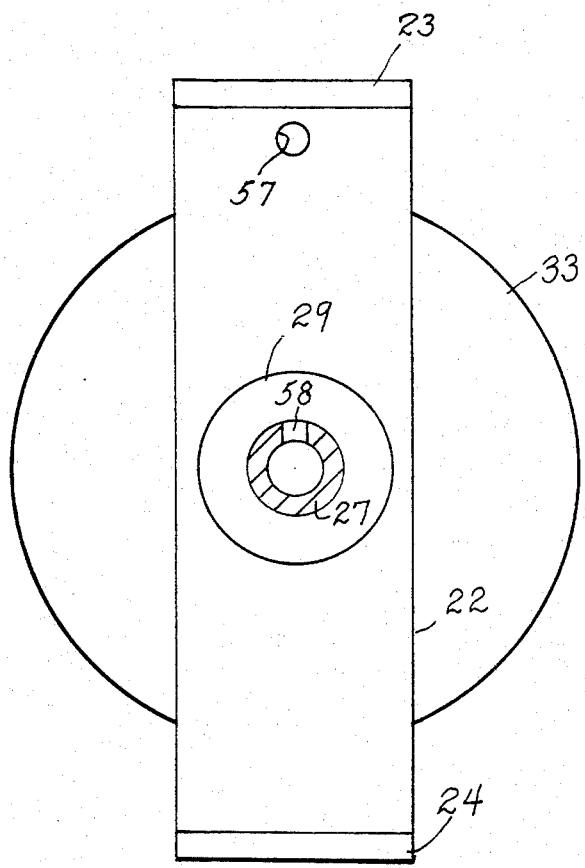
FIG. 4 is a transverse vertical cross-sectional view taken substantially on the line 4—4 of FIG. 1.

Referring to the drawings, 11 generally designates an improved countercurrent chromatography apparatus according to the present invention. The apparatus 11 comprises a base plate 12 on which are secured opposite parallel vertical upstanding wall members 13, 14, rigidly connected by a top plate 15. An electric motor 16 is secured horizontally to the upstanding vertical wall member 13 at the midportion thereof with its shaft 17 extending rotatably through a fixed bearing sleeve 18, the motor shaft 17 being rigidly secured perpendicularly to the center portion of a rotary arm 19 forming part of a generally rectangular rotary frame 20. Frame 20 comprises opposite parallel main rotary arms 21 and 22 whose ends are rigidly connected by respective horizontal elongated plate members 23 and 24. The opposite end portions of first-named rotary arm 19 are rigidly connected by horizontal bars 25 and 26 to main rotary arm 21 so that the rotary arms 19 and 21 are parallel to each other.

Designated at 27 is a coupling pipe which is journalled in upstanding wall member 14 by means of a bearing assembly 28 and which has an inner cuplike flange 29 which is rigidly connected to rotary frame arm 22 coaxially with motor shaft 17, whereby rotary frame 20 is rotatably supported between the upstanding fixed wall members 13 and 14 for rotation around the main horizontal axis defined by motor shaft 17 and coupling pipe 27.

Designated generally at 30 is a multi-layer coiled column assembly which is rotatably mounted in frame 20 for rotation around said main horizontal axis. Column assembly 30 comprises a spool having a shaft 31 and spaced circular flanges 32 and 33 rigidly and coaxially secured on reduced opposite end portions 34, 35 of shaft 31. Reduced shaft portion 34 is detachably coupled by a coupling sleeve 36 to a stub shaft 37 journalled centrally to rotary arm 21 by a bearing unit 38. Sleeve 36 is clampingly secured to shaft elements 34 and 37 by respective set screws 39, 39. The opposite reduced shaft portion 35 is centrally journalled in rotary arm 22 by a bearing unit 40. A tubular column 41 having a substantial number of superimposed layers is helically coiled on shaft 31 between the circular flanges 32, 33. The innermost (inlet) portion 42 of column 41 extends through a first aperture 43 provided in flange 32 near the main axis, and the outermost (outlet) portion 44 extends through an outer aperture 45 provided near the periphery of said flange 32.

A countershaft 46 is horizontally journalled in rotary arms 19, 21 by bearing units 47, 48. One end of countershaft 46 carries a toothed pulley 49 which is drivingly coupled by a toothed belt 50 to a fixed identical toothed pulley 51 rigidly secured on bearing sleeve 18. The opposite end of countershaft 46 carries a gear 52 which meshes with an identical gear 53 secured on shaft element 37.

Shaft element 37 is provided with an axially terminating passage 54 through which the respective inlet and outlet tubes 42, 44 extend. Said tubes 42, 44 also extend through an outer peripheral passage 55 in rotary arm 21, through a plurality of spaced, aligned sleeve-like supporting brackets 56 provided on elongated plate member 23, through an outer peripheral passage 57 in rotary arm 22, through an aperture 58 in coupling pipe 27, and through an axial guide sleeve 59 secured in a cup-like flange 60 rigidly secured to wall member 14, as shown in FIG. 1.

In operation, motor 16 directly drives rotary frame 20 around the main central axis of the apparatus via shaft 17. Countershaft 46 is rotated via toothed pulley 49, drive belt 50 and fixed pulley 51 at the same speed relative to frame 20. Shaft 31 and multi-layer coil assembly 30 are thus rotated at a rate twice that of rotary frame 20 and in the same direction relative to base 12, via identical gears 52, 53, shaft element 37 and coupling sleeve 36. The flow tubes 42, 44 are twist-free, as described in U.S. Pat. No. 4,321,138 to Y. Ito.

In each separation, the coiled column 41 is first filled with the stationary phase (either the upper or lower phase), followed by a sample charge via a sample port 61, shown diagrammatically in FIG. 1. Then, the mobile phase is pumped, via a pump 62, through the column while the apparatus is run at an optimum rate, typically between 50 and 150 rpm. The effluent through the outlet tube 44 is continuously monitored by a conventional UV monitor 63, and then fractionated into receptacles, such as test tubes, by a conventional fraction collector 64.

It will be noted that for effective operation, the column 41 comprising the multiple-layer coiled tubing is rotated in the proper direction according to the hydrodynamic motion of the two solvent phases in the coil. When the lower phase dominates at the head, this being the usual case, the column 41 is rotated in such a way that the internal terminal tube element 42 becomes the tail and the external terminal tube element 44 becomes the head. The rotation is reversed if the upper phase dominates at the head of the coil.

Since the frame 20 and the multi-layer column 41 simultaneously rotate in the same direction, both gravitational reversals of force and centrifugal forces are simultaneously developed in all the coil turns of the multiple-layer column 41. The coil turns, all mounted coaxially around the rotational axis with various helical diameters, all produce excellent peak resolution at the selected optimum rotational speed, due to a high retention level of the stationary phase.

Motor 16 is preferably of the adjustable-speed type, allowing continuously adjustable speed up to 400 rpm. As above mentioned, the multi-layer coil arrangement has a number of advantages over the previous CCC schemes utilizing a slowly rotating coil assembly. Because of the extremely large volume of the retained stationary phase, both peak resolution and the sample-loading capacity of the column are much increased. The continuous column is leak-free, is easily prepared, and is relatively inexpensive. The compactness of the column reduces the size of the apparatus, whereby to economize on cost and required space in the research laboratory.

The arrangement herein described can be readily scaled up for use in large-scale industrial applications.

While a specific embodiment of an improved continuous countercurrent chromatography apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. An apparatus for continuous countercurrent chromatography comprising a support, frame means journalled on said support for rotation around a substantially horizontal axis, separation column means comprising a multi-layer helically-coiled tubular column rotatably mounted on said frame means in multiple superposed coiled layers extending outwardly from said horizontal axis for rotation coaxially with said horizontal axis, inlet and outlet flow tubes connected to terminal ends of said multi-layer coiled column, and means to simultaneously rotate said frame means on the support and the multi-layer column on the frame means in the same direction, so as to simultaneously develop both gravitational force reversals and centrifugal forces in said multi-layer coiled column.

2. The apparatus of claim 1, and guide means on the support arranged to supportingly receive said inlet and outlet flow tubes, and means arranged to prevent twisting of said flow tubes as the frame means and multi-layer column simultaneously rotate coaxially.

3. The apparatus of claim 2, and wherein said rotating means is constructed to rotate said column at the same rate relative to the frame means as the frame means rotates relative to the support.

4. The apparatus of claim 2, and wherein said guide means includes first axial passage means for the flow tubes located adjacent one end portion of the frame means and second axial passage means for the flow tubes located on the support adjacent the opposite end portion of said frame means.

5. The apparatus of claim 1, and wherein said frame means comprises a substantially closed frame having opposite transverse rotary arms, said column having shaft means journalled between said arms, a motor mounted on the support and being directly drivingly connected to said frame means, countershaft means journalled in said frame means, and means drivingly coupling said motor to said column shaft means through said countershaft means.

6. The apparatus of claim 5, and wherein said motor is mounted substantially coaxially with the column shaft means.

7. The apparatus of claim 5, and wherein said countershaft means is journalled in said frame means in spaced parallel relation to the axis of said column shaft means.

8. The apparatus of claim 5, and wherein said coupling means includes stationary pulley means fixed to the support coaxially with said column shaft means, second pulley means on the countershaft means, belt means drivingly coupling said second pulley means to the fixed pulley means, and means gearingly coupling said countershaft means to said column shaft means.

9. The apparatus of claim 8, and wherein said first-named coupling means is constructed to drive the column shaft means at the same rotational rate relative to the frame means as the frame means rotates relative to the support.

10. The apparatus of claim 8, and wherein said stationary and second pulley means comprise identical toothed pulleys, and wherein said gearingly coupling means comprises respective meshing identical gears on the countershaft means and the column shaft means.

* * * * *